United States Patent [19]

Prestwich

[11] Patent Number: 4,544,504

[45] Date of Patent: Oct. 1, 1985

[54] REACTIVE PHEROMONE MIMICS FOR INSECT MATING DISRUPTION

[75] Inventor: Glenn D. Prestwich, Head of the Harbor, N.Y.

[73] Assignee: The Research Foundation of State University of New York, Albany, N.Y.

[21] Appl. No.: 566,516

[22] Filed: Dec. 29, 1983

[51] Int. Cl.[4] .............................................. C07C 57/02

[52] U.S. Cl. ................................ 260/408; 260/544 F

[58] Field of Search ............................ 260/408, 544 F

[56] References Cited

U.S. PATENT DOCUMENTS 3,679,720 7/1972 Siddall ................................ 260/408

3,991,108 10/1973 Jordan ............................ 260/544 F

FOREIGN PATENT DOCUMENTS 710843 6/1965 Canada .

OTHER PUBLICATIONS

Seel et al., *Chemische Berichte*, 91, No. 12, p. 164, 1958.

*Primary Examiner*—Charles F. Warren
*Assistant Examiner*—Elizabeth A. Flaherty
*Attorney, Agent, or Firm*—Omri M. Behr

[57] ABSTRACT

It has been found that the acyl fluorides corresponding to aldehydes which have a sex attractant effect upon certain insects, in particular but not limited to those of the genus Lepidoptera, cause occurrence of the hyperagonist effects in males of the appropriate species wherein the claspers and genitalia were extended irreversibly and the upwind flight towards pheromone sources is disturbed by rapid out-of-plume motions. This effect is most useful in disruption of mating patterns. There are also provided certain novel acyl fluorides having the foregoing properties.

8 Claims, No Drawings

REACTIVE PHEROMONE MIMICS FOR INSECT MATING DISRUPTION

BACKGROUND OF THE INVENTION

It has been known for several years that certain saturated, mono- and di- unsaturated aldehydes of chain length between about 6 and about 20 carbon atoms, especially those having an even number of carbon atoms between 12 and 18, exhibit sex attractant properties for certain insects, in particular, Lepidoptera and certain beetles.

Generally speaking, it has been found that the mono unsaturated aldehydes wherein the double bond is in the Z or E orientation are specific attractants either per se or in combination with compounds of similar structure for a substantial number of a particular species. This property has been used in the ecologically sound approach of insect control by trapping or disorientation. The approach has become so well accepted that a number of these aldehydes are commercially available.

A sample list (though not exclusive) is set forth hereinbelow in Table I. Certain abbreviations will be employed hereinbelow, namely, the indication Z9, E11, -16:ALD (or ACF) indicates (Z,E)-9,11-hexadecadienal or (Z,E)-9,11-hexadecadienoyl fluoride respectively.

TABLE I

Commercially available Aldehyde pheromones and pest insects controlled.*

| Common name | Latin name | Commercial attractant or pheromone |
|---|---|---|
| Leptoptera | | |
| Sugarcane borer | (*Diatraea saccharalis*) | Z9, E11-16: ALD |
| Navel Orange worm | (*Amylois transitella*) | Z11, Z13-16: ALD |
| Artichoke Plume moth | (*Platyptilia carduidactyla*) | Z11-16: ALD |
| Cranberry Girdler | (*Crambus topiarius*) | Z13-18: ALD |
| Pickleworm moth | (*Diaphania nitidalis*) | E11-16: ALD |
| Rice Stein-borer/Cranberry Girdler | (*Chilo suppressalis*)/ (*Crambus topiarius*) | Z13-18: ALD Z7-14: ALD |
| Olive moth | | |
| Spruce budworms | (*Choristoneura fumiferana, O. occidentalis*) | E11-14: ALD Z11-14: ALD |
| Tobacco budworm, cotton bollworm, etc. | (*Heliothis virescens, H. zea, H. armigera, H. phloxiphaga*) | Z11-16: ALD Z9-16: ALD Z7-16: ALD Z9-14: ALD 16: ALD 14: ALD |
| Coleoptera | | |
| Boll weevil | (*Anthonomus grandis*) | 3,3-dimethyl-Δ1,α-cyclohexane-acetaldehyde |
| Grain and stored product beetles | (*Trogoderma granarium*) *T. inclusum, T. glabrum* | E8-14-$CH_3$; 16: ALD Z8-14-$CH_3$, 16: ALD |

*The notation Z9, E11-16: ALD indicates (Z,E)-9,11-hexadecadienal.

A further listing of aldehydes and their attractant effects on certain insects, in particular but not limited to Lepidoptera will be found in the article by M. Inscoe in Kydonieus and Beroza, Insect Suppression with Controlled Release Pheromone Systems (CRC Press, Boca Raton, 1982), volume 2, at page.

The use of acyl fluorides of moderate chain length for any purpose has not heretofore been reported with one exception. German OLS No. 2108576 reports that certain moderate chain length highly branched mono-olefinic acyl fluorides are useful in insecticides at concentrations of 4.8 to 20 $Kg/m^3$. This concentration is of course vastly greater than that necessary to bring about a sex attractant effect.

Methods of oxidizing aldehydes to the corresponding acids without interference with any unsaturation which may be present are of course well known in the art. Several methods have also been reported for the conversion of alkanoic and alkenoic acids to the corresponding acyl fluorides. The reaction of acyl chlorides with pyridinium polyhydrogen fluoride is reported by Olah et al., (J. Org, Chem., 44, 3872 (1979)). Another route which comprises treating the acid with potassium fluorosulfonate was reported by Seel and Langer (Chem. Ber., 91, 2553 (1958)). Yet another, though less convenient mode is that reported by Siddall in German OLS No. 2108576, in which the acid is converted into the corresponding acid chloride by means of thionyl chloride and the product subsequently fluorinated with hydrogen fluoride. Yet another method is disclosed by Olah, et al., which comprises reacting the appropriate acid with cyanuric fluoride in acetonitrile in the presence of pyridine. (Synthesis 4, 87 (1973).

SUMMARY OF THE INVENTION

It has been found that aldehydes which have a sex attractant effect upon male insects, in particular but not limited to those of the genus Lepidoptera, when converted into the corresponding acyl fluoride that is to say, where the hydrogen of the aldehyde is replaced with fluorine, are turned into hyperagonists.

The effect upon the male is no longer that of a simple sex attractant but can cause irreversible extension of the claspers and genitalia and rapid, upwind flight out of the odor plume. The mechanism of such activity is not clear but is believed to relate to a tighter binding to the receptor protein or to interference with the clearing of the pheromone (or analog) from the receptor.

The aldehydes which act as species specific sex attractants are usually alkenals or alkadienals wherein the unsaturation is not conjugated with the carbonyl oxygen of the aldehyde. Such compounds are more expensive to produce than the corresponding saturated aldehydes and the alpha, beta unsaturated aldehydes. These two later classes of compounds are not quite as efficient as attractants as the species specific unconjugated, unsaturated aldehydes, nevertheless, they may have an acceptable of level of activity.

The hyperagonist activity of the acyl fluorides of the present invention has not heretofore been recognized or suggested. However, some compounds within the scope of the method of use claims of the present invention are known. Among these may be mentioned the acyl fluorides of moderate chain length alkanoic acids and two alkenoyl fluorides. Apart from these compounds all of the compounds pertaining to the present invention are novel compounds.

The acyl fluorides of the present invention have a fairly good resistance to hydrolysis in atmospheric conditions in contrast to the corresponding acyl chlorides or bromides which are less volatile and which hydrolyze more rapidly in the presence of moisture. The method of utilizing the compounds of the present invention includes placement in traps, formulation in atmospherically stable carriers such as oils, gums, plastics, rubber, or adhesive emulsions and the like as well as encapsulation in microcapsules. This latter form is particularly desirable where an extensive area is to be treated. The microcapsules can be produced by conventional means and broadcast whether in their ordinary form or when coated with an adhesive layer so as to adhere to the foliage of the location into which they are broadcast.

The active material (acyl fluoride) is broadcast into the appropriate area in any of the above formulations at between 1 and 10,000 times the concentrations required for eliciting attractant response in the males by the corresponding aldehyde, although the actual quantities utilized are probably no more than 10 times the amounts of pheromone used in the field. In a preferred mode there are broadcast between 0.1 and 1000 mg/$m^2$ of ground surface area to be treated.

An appropriate aldehyde may be converted into the corresponding acid by mild oxidation. It has been found that silver oxide in alkaline ethanol is a suitable oxidizing agent. Similarly, the corresponding alcohol may be oxidized to the acid with pyridinium dichromate in dimethylformamide.

The acid is converted to the corresponding acyl fluoride by one of the several synthetic methods set forth above. For example, as a fluorinating agent there may be employed a 100% excess of hexafluoropropyldiethylamine in ether. The reaction is carried out at ambient temperature and is substantially instantaneous. The corresponding N,N-diethyltetrafluoropropionamide produced in the reaction is removed by distillation under reduced pressure with moderate heating to leave the desired acyl fluoride in high yield as a residue which may be further distilled in vacuo to obtain higher purity.

DESCRIPTION OF THE PREFERRED EMBODIMENTS

The active compounds of the present invention are the acyl fluorides corresponding to aldehydes having sex attractant properties for insect males.

The compounds have the general formula R.C(F)=O wherein R is alkyl, alkenyl, methyl alkenyl, alkadienyl, or gemdimethylcyclohexanyl lower alkenyl wherein the term "alk" represents a straight carbon chain of, suitably, 6 to 20 carbon atoms and "lower alk" is a carbon chain of 1 to 4 carbon atoms.

The most active parent compounds, that is to say, the aldehydes and therefore the most active acyl fluorides are those wherein R contains between 9 and 17 preferably 11, 13, 15 or 17 carbon atoms. These compounds generally contain an unconjugated double bond either in the Z or E orientation on the central portion of the chain. This double bond may be conjugated with another double bond. Generally, the double bond is not conjugated with the terminal carbonyl oxygen.

Notwithstanding preference for the foregoing compounds, compounds which are either fully saturated, have an isolated double bond at the end of a chain away from the carbonyl group, or conversely have one or two double bonds conjugated with carbonyl oxygen are nevertheless, to be considered to fall within the scope of the present invention.

Many alkanoyl fluorides are known but their use in the manner disclosed and claimed in the present invention has not heretofore been known. All of the other compounds of the present invention with the exception of 10-undecenoyl fluoride and 9-octadecenoyl fluoride are new compounds.

While the scope of the present invention is in no way to be considered limited thereto certain acyl fluorides are particularly to be preferred. These are: (Z)-7-or 9-dodecenoyl; (Z)-5-tetradecenoyl; (Z)-7- or 9-tetradecenoyl; (Z) -11-tetradecenoyl; (E)-11-tetradecenoyl; (Z)-7,8,9,11 or 13-hexadecenoyl; (E)-11-hexadecenoyl; (Z)-14-methyl-8-hexadecenoyl and (E)-14-methyl-8-hexadecenoyl; (Z)-11,13 hexadecadienoyl; Z-(9,11) hexadecadienoyl; (Z)-13-octadecenoyl and 3,3,-dimethyl $\Delta\alpha$ cyclohexane acetyle, fluorides.

The compounds of the present invention may be prepared from the corresponding aldehyde or acid by various routes. The oxidation of the aldehyde to the acid is accomplished by a mild oxidizing agent. A slight excess of silver oxide (formed from silver nitrate in ethanol in the presence of aqueous sodium hydroxide) is particularly suitable.

In this procedure the aldehyde and silver nitrate are taken up in aqueous ethanol (2:1) and a large excess of aqueous sodium hydroxide slowly added thereto at ambient temperature. The mixture is agitated for about an hour, the ethanol removed in vacuo and the residue diluted with ether and water. The ether layer is then dried in the usual manner, volatiles removed and the residue purified, suitably by flash chromatography with hexane/ethyl acetate/acetone to yield the appropriate acid.

In an alternative method for the preparation of acids starting from the alcohols there is employed a method of Corey and Schmidt (*Tet. Lett.*, (1979), 399). The appropriate alcohol is taken up in distilled dimethylformamide and a seven-fold excess of pyridinium dichromate added thereto. The reaction mixture is stirred at room temperature for about 10 hours, a further equivalent of pyridinium dichromate is added and the reaction stirred for a further 10 hours. The mixture is quenched in a large excess of water, extracted with a water immiscible solvent suitably diethylether, dried, and the solvents removed in vacuo to yield the acid as a residue. The acid is then purified suitably by chromatography on silica gel.

Laboratory Evaluation of Z-9-Tetradecenoyl fluoride (Z-9-TDA-F) and Z-11-Hexadecenoyl fluoride (Z-11-HDA-F)

Methods:

Male *H. virescens* moths (2–3 days old) were exposed in pint cartons to atmosphere presumed saturated with the test compounds in vapor form. The compounds were deployed singly (or combined) at a dosage of 10 mg active ingredient/100 microliters of hexane. These treatments were applied on filter paper and presented to 10 male moths/carton for a set period of 24 hours. The cartons were sealed during the 24-hr. treatment periods. After this exposure, 50 treated males/test (and 25 untreated (CK) sibling males) were paired singly with untreated females (2–4 days old) in 1-gallon cartons, fed 10% sucrose solution, and held for 5 days. After this period, females were dissected, and mating success was determined by tabulating the numbers of spermatophores found in the females that were passed to them from the treated (or untreated) males. Also, direct visual observations regarding the behavior of the moths, treated and untreated, were denoted and herewith reported.

Tests were run as follows: Z-9:14:ACF; Z-11-16:ACF; Z-9-14 ACF+Z-11-16:ACF; and Z-9-TDA-F+Z-11-HDA-F.

Results

Direct observations made at the time when the chemicals were placed into the treatment cartons (10 male moths/carton) revealed the Z-9-14:ACF caused an immediate physical, whole body response by the males. This response was sexually oriented: claspers and genitalia were extended, seemed locked outside the terminal abdominal segment, and were not retracted during or after the treatment period for any significant time span. When the filter papers were placed in the treatment cartons, the male moths immediately fluttered their wings, extended the reproductive organs, and became generally hyperactive in obviously atypical active flight and sexual response sequences, such as they might react to an aphrodisiac. When these treated males were transferred and paired singly with untreated female partners, their claspers remained extended and seemed locked in place (exposed) during the subsequent 5-day mating period. This hyperactive response was seen in 90% of the treated males.

When the Z-11-16:ACF treatment was applied, no sexual behavior or hyperactivity was seen, but the behavior was typical; moths were sedate, claspers were not extended, and no wing flutter was noted.

When the combination Z-9-14 ACF+Z-11-ACF treatment was deployed, about 40% of the male moths reacted as those treated previously with only Z-9-ACF. However, these treated males did not persist in extension of the claspers when they were transferred to cartons with females.

Significantly fewer fertile eggs were laid by females paired with males exposed to the combined chemicals (<30 eggs/female) compared with numbers laid by the check groups (>150 eggs/female) that hatched. However, no significant differences were seen in numbers of fertile eggs laid by females paired with males treated with either of the single compounds when numbers were compared with numbers laid by the respective check groups.

The only obvious difference in the average numbers of spermatophores/female was a reduction found in females mated with males treated with Z-11-16:ACF.

Conclusions:

Z-9-14:ACF is an aphrodisiac to male *H. virescens* as dosages presented and for deployment time periods.

Windtunnel experiments using the acyl fluorides in a natural 15:1 Z11-16:ACF to Z9-14:ACF ratio showed significant effects on flight behavior.

Experiment:

Four to six-day old males isolated from females as adults on a 16:8 L:D cycle were placed in individual galvanized wire mesh cylinders, 6 cm long×6 cm diameter with one open end. Males wer acclimated to conditions in the 3.6×1×1 m wind tunnel (0.5 m/sec wind velocity, 24°+3° C., 0.3 lux light intensity) for ca. 30 min and testing then began ca. 5 hrs after lights off. Methylene chloride solutions of ACF's and ALD's were made at 10μg/μ1 strengths for the the Z11-16:ACF and Z11-16:ALD. Ratios of Z11-16 to Z9-14 compounds in solution were 15:1. The ends of 1 cm-long cotton dental wicks were impregnated with 10μl of the test mixture and placed on a galvanized steel platform 15 cm above the floor. Individual males in their cylinders were then placed into the odor plume 2.9 m downwind of the source and their responses recorded. For some experiments, males were pre-exposed for 15 minutes to 2 wicks impregnated with either the ACF's of ALD's by placing the males' screen cylinders in rows of 10 males in the plumes immediately downwind of the sources. Males were then tested from 0–10 min after the end of exposure for their responses to the 15:1 mixture of ALD's as per the procedure described above. When pre-exposed to the ALD's, 41%, 34%, and 14% of the 29 males flew upwind in the plume, flew upwind to within 30 cm of the source, and touched the source, respectively, significantly lower than with no pre-exposure (82%, 66%, and 39%, respectively; N=38). Pre-exposure to the ACF's resulted in no significant reduction (65%, 55%, 26%; N=31).

Conclusions:

Forty-five percent of the 51 males tested locked onto and flew upwind in the plume. However, only 10% made it to within 30 cm of the source, which was located by only a single male. The low numbers of close approaches qualitatively seemed to be due to the males's uncommonly rapid, straight flight trajectories which caused them to lose the plume. They appeared to have much greater linear velocity and lower angular velocity (zigzagging) than those to the 15:1 mixture of aldehydes. Thirty-five percent of the males (N=34) located the aldehyde source and 76% flew within 30 cm of it. Males which did not fly in the plume of the ACF mixture exhibited an unusually rapid, straight-upwind take-off at ca. a 45° angle toward the ceiling, in contrast to normal "non-responders" which usually fly straight up of the cylinder to the ceiling with no upwind displacement. Two-compound blends in which the Z9-14:ACF and Z9-14-ALD were switched elicited responses from males not significantly different from 0, except for the blend with Z11-16:ACF plus Z9-14:ALD which evoked brief upwind flights in the plume from 19% of the males.

EXAMPLE I

1-Fluoro dodecanoic Acid

To a solution of 1-fluorododecanol (112 mg., 0.55 m mole) in distilled dimethyl formamide (2 ml) was added pyridinium dichromate (PDC) (723 mg., 3.5 equivalents). The reaction mixture was stirred at room temperature 10 hours and then more pyridinium dichromate (100 mg) was added and the reaction mixture stirred for 10 hours more. The mixture was poured into 10–20 volumes of water and extracted with diethylether (3 times). The extracts were combined, washed with brine and dried (over anhydrous magnesium sulfate); the solvents were removed in vacuo and the crude acid (70 mg) was chromatographed on 3 g. of 230–400 mesh silica gel by elution with hexane/ethyl acetate/acetone (8:2:0.5) to give 1-fluorododecanoic acid (40 mg.)

In accordance with the above procedure but where in place of 1-fluorododecadecanol there is utilized tetradecan-1-ol or hexadecan-1-ol there are obtained the corresponding alkanoic acids.

In accordance with the foregoing procedures but where, in place of 1-fluorododecanol there is utilized (Z)-7-dodecenol; (Z)-9-dodecenol; (Z)-5-tetradecenol; (Z)-7-tetradecenol or (E)-11-tetradecenol there are obtained the corresponding (Z)-7-dodecenoic, (Z)-9-dodecenoic, (Z)-5-tetradecenoic, (Z)-7-tetradecenoic, (Z)-11-tetradecenoic or (E)-11-tetradecenoic acids respectively.

EXAMPLE II

Palmitoyl Chloride

Palmitic acid (1 mole) is heated with thionyl chloride (20 mole) at 75° C. for 2 hours. The thionyl chloride is removed by distillation at atmospheric pressure and the palmitoyl chloride is then separated by distillation under reduced pressure.

In accordance with the above procedure but where in place of palmitic acid there are utilized any of the alkanoic of alkenoic acids produced in accordance with Example I, there are obtained the corresponding acid chlorides.

EXAMPLE III

Palmitoyl Fluoride

Palmitoyl chloride (651 mg, 2.2 mole) was added to pyridinium poly(hydrogen fluoride) (1 ml) in a teflon reaction vial and the mixture stirred at 20° C. for 20 min. After cooling to 0° C., it was quenched with ice-water (5 ml), extracted with ethyl acetate, and the organic layer washed (water, brine), dried over anhydrous magnesium sulfate, concentrated and evaporatively distilled (120° C./0.025 torr) to give palmitoyl fluoride (76%) (contaminated with 5% of the corresponding acid). Since this concentration of contaminant is not harmful to the biological activity of the compound, no further purification is required.

In accordance with the foregoing procedures, but utilizing in place of palmitoyl chloride, any of the other acid chlorides prepared in accordance with Example II, the corresponding acid fluorides are obtained.

EXAMPLE IV

10-Undecenoyl Chloride

10-Undecenoyl chloride (190 mg) and $KSO_2F$ (200 mg), (prepared from $SO_2$ and KF under pressure) was heated at 80° for 30-45 min. The crude acid fluoride was purified by evaporative distillation into a chilled receiver to yield pure 10-undec-1-enoyl fluoride (bp ca. 80°/0.05 mm Hg).

In accordance with the above procedure but starting with (Z)-7-dodecenoyl chloride, there is obtained the corresponding (Z)-7-dodecenoyl fluoride.

EXAMPLE V

Oleoyl Fluoride

To a solution of cyanuric fluoride (16 g, 0.12 mole in acetonitrile (125 ml) was added within 10 mins. a solution of oleic acid (80 g., 0.30 mole) and pyridine (24 g., 0.3 mole) in 125 ml. acetonitrile. The reaction mixture was stirred for 50 min and poured into ice-water, extracted with ether, and the organics dried over sodium sulfate. Removal of solvent and distillation in vacuo afforded oleoyl fluoride (85%, bp 184–186/12 torr).

In accordance with the above procedure but with, in place of oleic acid there is utilized as starting material (Z)-7, 8, 9 or 12 hexadecenoic acid, (E)-11-hexadecenoic acid, (Z)-14-methyl-8-hexadecenoic acid or (E)-14-methyl-18-hexadecenoic acid, there are obtained the corresponding acid fluorides.

EXAMPLE VI

To a solution of 3,7,7,11,11-Pentamethyldodec-2-enoic acid (0.5 g) in benzene (5 ml) was added thionyl chloride (1 g). The mixture was stirred for 2 hrs. at 20°–60° C. to complete acid chloride formation. The solution was then cooled to −5° to 0° C. while anhydrous gaseous hydrofluoric acid was bubbled in. The solution was allowed to stand for 2 hours at room temperature, the surplus hydrofluoric acid removed by addition of solid sodium fluoride, which was removed by filtration and the acyl fluoride isolated by distillation in vacuo.

EXAMPLE VII

Z-9-tetradecenoic Acid

To a solution of Z-9-tetradecenal (1.177 g., 5.61 mmol) and silver nitrate (1.049 g, 6.17 mmol) in ethanol/$H_2O$, (15 ml, 2:1) was added a solution of sodium hydrochloride (1.055 g., 26.4 mmol) in water (10 ml), dropwise at room temperature. After stirring for 1 hr., the mixture was filtered, the ethanol removed in vacuo and the residue diluted with ether (100 ml). Additional water (25 ml) was added and the aqueous layer was acidified with aqueous sulfuric acid and extracted with ether. The layer was dried over anhydrous magnesium sulfate, the volatiles removed and the crude product purified by flash chromatography using hexane/ethyl acetate/acetone, 8/2/1, to give 0.9785 g. (77.3%) of the acid; Rf (H/EA/A, 7/3/1)=0.61; IR (film) 2750–3300 (COOH), 2850–3000 (alkane, alkene C—H), 1726 cm-1 (C═O); H NMR ($CDCl_3$)=0.94 (t,J=6Hz,3H) 1.18–1.50 (br s, 14 H), 2.06 (br d, J=6Hz, 4H),2.37 (t, J=7Hz, 2H), 5.32 (t, J=qHz, 2H), 10.6–10.8 (br s, 1H).

In accordance with the foregoing procedure but where, in place of starting with Z-9-tetradecenal there is employed (Z)-13-octadecenal or 3,3-dimethylcyclohexylidene acetaldehyde, there are obtained the corresponding (Z)-13-octadecenoic and 3,3-dimethylcyclohexylidene acetic acids.

EXAMPLE VIII

Z-9-tetradecenoyl Fluoride

To the fluorinating agent, 1,1,2,3,3,3-hexafluoro-1-propyldiethylamine (1.070 g, 4.94 mmol) was added Z-9-tetradecenoic acid (0.500 g, 2.21 mmol) in ether (1.0 ml) dropwise at 25° C. The ether was removed by a stream of nitrogen and the mixture was heated at 60° C. for 2 hrs. After cooling to 25° C. the mixture was diluted with ether (200 ml) and the ether layer was washed with water, brine and then dried over anhydrous magnesium sulfate. The solvent was removed in vacuo and the mixture was subject to distillation. The side product from the fluorinating agent, N,N-diethyl-2,3,3,3-tetrafluoropropionamide came out at 80°–90° C. oil bath, 0.1 mm Hg. (temp. unknown) and the remaining residue was evaporatively distilled to give 434 mg (85%) of the acyl fluoride as a clear colorless liquid, Rf (H/EA, 8/2)=0.81; IR (film) 2850–3100 (alkane, alkene CH), 1840 (C═O); HNMR ($CDCl_3$), 0.90 (t, J=6HZ, 3H), 1.20–1.45 (m, 14H), 2.05 (br d, 4H), 2.52 (t, J=6HZ, 2H), 5.33 (t, J=6HZ, 2H).

In accordance with the foregoing procedure but where in place of (Z)-9-tetradecenoic acid there is utilized (Z)-13-octadecenic acid or 3,3-dimethylcyclohexylidene acetic acid, there are obtained the corresponding acyl fluorides.

EXAMPLE IX

(Z)-11-hexadecenoic Acid (Z)-11-hexadecenoic acid was prepared as described in Example VII but starting with Z-11-hexadecenal (1.115 g, 4.68 mmol) and (0.875 g, 5.15 mmol) in 15 ml. of ethanol/water, 2/1, and NaOH (0.880 g, 22 mmol) in water (10 ml); purification by flash chromatography (H/EA/A), 8/2/1, gave 0.478 g (40%) of the acid; Rf (H/EA,7/3), 0.64; IR (film) 2800–3300 (CODH), 2850–2950 (alkane, alkane C—H), 1700 $cm^{-1}$ (C═O), $^{1}H$ NMR 0.95 (t, J=6 HZ, 3H), 1.20–1.50 (br S, 18 H), 2.05 (br d, J=6 HZ, 4H), 2.38 (t, J=6HZ, 2H), 5.32 (t, J=6HZ, 2H), 10.6–10.8 (br S, 1H).

EXAMPLE X

(Z)-11-hexadecenoyl Fluoride (Z)-11-hexadecenoyl fluoride was prepared as described in Example VIII using 0.350 g. (1.38 mmol) of (Z)-11-hexadecenoic acid in ether acid in ether (2 ml) and 0.334 g. (1.54 mmol) of 1,1,2,3,3,3-hexafluoro-1-propyldiethylamine. After removing the solvent and side product from fluorinating agent, the crude residue was evaporatively distilled to give 278.3 mg (79%) of the acyl fluoride; Rf (H/EA 8/2)=0.71; IR (film) 2850–3000 (alkane, alkene CH), 1840 $cm^{-1}$ (C═O), H NMR ($CDCl_3$) 0.92 (t, J=6 HZ, 3H), 1.15–1.40 (bs, 18 H), 2.03 (br d, J=6 HZ, 4H), 2.52 (t, J=7HZ, 2H), 5.35 (t, J=6HZ, 2H).

Formulation Techniques

The acyl fluoride is formulatable in controlled release formulations in utilizing the same technology employed for the corresponding aldehyde pheromones. Both aldehydes and acyl fluorides are ultimately subject to air and light induced conversion to the acids and other degradation products. The commercially available Hercon ® plastic (PVC) laminated dispenser, the Conrel ® fiber, simple rubber septa, dental cotton wicks, or the simple PVC plastic "tip protector capsules" disclosed by Hendricks, (J. Econ. Entomol, 11, 1005 (1982)) may be employed. Also applicable are the methods of E. R. Mitchell, (ed. "Management of Insect Pests with Semiochemicals", Plenum Press, NY, 1981) and Kydonieus, A.F., and Beroza, M., Ed. ("Insect Suppression with Controlled Release Pheromone Systems.", CRC Press, Boca Raton, 1982.) Said disclosures being incorporated herein by reference.

Formulation 1:

The capsules were constructed from two bullet-shaped wire tip protectors made of molded PVC (product of Sinclair and Rush., St. Louis, Mo.). Two sizes of the tip protectors (no. 0.093-6, 2.36 mm ID by 9.5 mm inside length and no. 0.112-6, 2.85 mm ID by 9.5 mm inside length) were joined together (one into the other) at their open ends to make a completely closed capsule. Outside dimensions of the assembled PVC capsule were ca. 4.2 mm OD by 17 mm long. Thickness of the capsule wall was ca. 0.73 mm. The capsules were loaded with dosages of acid fluorides by inserting the needle of a 50 μl syringe into the joint of the capsule halves. A hole was not made through the capsule wall. Thus, by injection, the appropriate formulation was applied inside the hollow capsules where the reservoir of chemicals was protected from ultraviolet radiation and excessive atmospheric oxygen.

Formulation 2:

Laminated plastic (Hercon) pheromone bait dispensers were procured from commercial sources. These acid fluorides were loaded at a concentration of 40 mg/2.54 $cm^2$ in the commercially prepared Hercon laminated PVC material, 1.39 mm thick. This laminated dispenser was prepared with an adhesive matrix (CX) containing the measured dosage of pheromone components layered between two sheets of PVC plastic.

I claim:

1. A compound of the formula R.C(F)═O wherein R is alkenyl, methylalkenyl, or alkadienyl having a straight-chain alk chain of 6 to 20 carbon atoms or gem-dimethylcyclohexyl lower alkenyl having a lower alk chain of 1 to 4 carbon atoms, provided that where R.C(F)═O is undecenoyl fluoride the double bond is other than Δ10 and where R.C(F)═O is octadecenoyl fluoride the double bond is other than Δ9.

2. A compound of claim 1 wherein R is alkenyl of 9 to 17 carbon atoms.

3. A compound of claim 2 wherein the double bond is at 5, 7, 9, 11 or 13, provided such positions are present.

4. A compound of claim 1 wherein R is alkadienyl of 9 to 17 carbon atoms.

5. A compound of claim 1 wherein the double bonds are conjugated with respect to each other.

6. A compound of claim 2 wherein the double bond is conjugated with the acyl carbonyl group.

7. A compound of claim 1 wherein R—C═O is (Z)-7 or 9-dodecenoyl; (Z)-5,7,9 or 11-, or (E)11-tetradecenoyl; (Z)-7,8,9,11, or 12- or (E)-11-hexadecenoyl; (E) or (Z)-14-methyl-8-hexadecenoyl; (Z)-(11,13) or (9,11)-hexadecadienoyl; (Z)-13-octadecenoyl 3,3-dimethyl Δ1α cyclohexane acetyl; or E(2)-tetra, hexa- and octadecenoyl.

8. A compound of claim 4 where the double bonds are at two of the 9, 11, 13 or 15 position, provided such positions are present.

* * * * *